United States Patent [19]

Kurihara et al.

[11] Patent Number: 5,178,899
[45] Date of Patent: Jan. 12, 1993

[54] METHOD FOR PROCESSING TASTE-MODIFIER

[75] Inventors: Yoshie Kurihara, 4-7, Okuzawa 7-chome, Setagaya-ku, Tokyo 125; Hiroshige Kohno, Tokyo; Masaaki Kato, Tokyo; Kenji Ikeda, Tokyo; Masako Miyake, Tokyo, all of Japan

[73] Assignees: Yoshie Kurihara; Asahi Denka Kogyo Kabushiki Kaisha, Tokyo, Japan

[21] Appl. No.: 651,060

[22] Filed: Feb. 5, 1991

Related U.S. Application Data

[63] Continuation of Ser. No. 362,877, Jun. 7, 1989, abandoned.

[30] Foreign Application Priority Data

Jun. 21, 1988 [JP] Japan .................................. 63-153143
Nov. 2, 1988 [JP] Japan .................................. 63-277717
Nov. 11, 1988 [JP] Japan .................................. 63-285476

[51] Int. Cl.$^5$ ............................................ A23L 1/221
[52] U.S. Cl. ..................................... 426/655; 426/615; 426/638; 426/650; 426/534; 426/427; 426/640
[58] Field of Search ............... 426/615, 638, 650, 534, 426/655, 627, 640

[56] References Cited

U.S. PATENT DOCUMENTS 3,969,183 7/1976 Redd ................................ 426/471 X
4,113,865 9/1978 Dondi et al. ...................... 426/599 X
4,587,132 5/1986 Fuller .................................. 426/640

FOREIGN PATENT DOCUMENTS 0003911 9/1979 European Pat. Off. .
2089624 1/1972 France .
2315864 1/1977 France .
1506052 4/1978 United Kingdom .
2185674 7/1987 United Kingdom .

OTHER PUBLICATIONS

G. Penso: "Index Plantarum Medicinalium Totius Mundi Eorumque Synomymorum", 1984, O.E.M.F., Milano, IT * p. 294, lines 31–36.
Commonwealth Agricultural Bureau, abstract 0206272, 7C010–01239, OC054–06355m 7W010–01239, Lim–Ho. Chee Len: "Tissue Culture of *Curculigo latifolia* Dry. ex W. T. Ait (Hypoxidaceae)".
Gardens' Bulletin, 1981, 34(2), * Abstract *.
Chemical Abstracts, vol. 107, 1987, p. 455, abstract 194889t, Columbus, Ohio, US, J. Xu et al.: "Chemical Constituents of Xianmao (*Curculigo orchioides*), I. Isolation and Characterization of curculigine A".
Zhongcaoyao, 1987, 18(5), 194–5, 222 * Abstract *.

*Primary Examiner*—Joseph Golian
*Attorney, Agent, or Firm*—Frishauf, Holtz, Goodman & Woodward

[57] ABSTRACT

A method for processing a taste-modifier which comprises formulating a taste-modifier comprising fresh *Curculigo latifolia* fruits, dried fruits thereof or a curuculin-containing material obtained therefrom into granules or a film, thus stabilizing said taste-modifier and effectively utilizing the taste-modification effect of the same.

9 Claims, No Drawings

# METHOD FOR PROCESSING TASTE-MODIFIER

This application is a continuation of application Ser. No. 07/362,877, filed Jun. 7, 1989 (abandoned).

BACKGROUND OF THE INVENTION

1. Field of the Invention

This invention relates to a method for processing a taste-modifier. More particularly, it relates to a method for processing a taste-modifier comprising fresh curculigo *latifolia* fruits, dried fruits thereof or a curuculin-containing material obtained therefrom into a stable form suitable for effectively exhibiting the taste-modification effect of the same.

2. Description of the Prior Art

Known taste-modifiers, which affect the receptor membranes on the tongue in such a manner as to modify the taste of a food, include those which remove the sweetness of a sweet food in the mouth, for example, gymnemic acid contained in *Gymnema sylvestre* leaves and ziziphine contained in *Ziziphus jujuba* leaves; and those which convert the sourness of a sour food into sweetness in the mouth, for example, miraculin contained in *Synsepulm dulcificum* fruits.

It is further known that *Curculigo latifolia* fruits, which grow in Western Malaysia and the southern part of Thailand and belong to the genus Curculigo of Amaryllidaceae, are good to eat and exhibit an appetizing effect.

Although miraculin has the abovementioned effect, it is not put into practical use as a taste-modifier because of its poor stability.

No effect of *Curculigo latifolia* fruits except the abovementioned one has been known so far.

The present inventors have found that a sour material or water taken after eating *Curculigo latifolia* fruits would taste sweet. Thus they have attempted to identify the sweetness-inducer. As a result, they have found that a specific protein contained in *Curculigo latifolia* fruits is the aimed sweetness-inducer (cf. Japanese Patent Application No. 153143/1988). This protein is named curuculin. In order to utilize this curuculin as a taste-modifier on a commercial scale, it is required to obtain said taste-modifier by as a simple method as possible. It is further required to process said taste-modifier into a stable form suitable for effectively exhibiting the taste-modification effect.

Pure curuculin may be obtained by washing fresh *Curculigo latifolia* fruits or dried fruits thereof with water, extracting them with an aqueous solution of a salt and purifying the extract by ion-exchange chromatography with the use of CM-Sepharose and HPLC with the use of a gel column. Pure or almost pure curuculin would remain stable for a month or longer in the form of an aqueous solution at room temperature. However fresh *Curculigo latifolia* fruits, dried fruits thereof or crude curuculin, in particular, in the form of an aqueous solution, would have a poor stability upon storage since they are contaminated with proteases and bacteria contained in the *Curculigo latifolia* fruits. In addition, it is highly difficult to harvest a large amount of *Curculigo latifolia* fruits, since a *Curculigo latifolia* fruits, which has an ovoid figure with a process on the top, is as small as 1 cm in diameter and weighs only 1 g even in a fully ripened state. Thus it has been required to establish a method for efficiently obtain the taste-modifier comprising *curculigo latifolia* fruits, dried fruits thereof or a curucular-containing material obtained therefrom and to minimize the amount of the starting *Curculigo latifoblia* fruits in order to utilize said taste-modifier on a commercial scale.

SUMMARY OF THE INVENTION

It is an object of the present invention to provide a method for processing a material comprising *Curculigo latifolia* fruits, dried fruits thereof or a curuculin-containing material obtained therefrom into a stable form suitable for effectively exhibiting the taste-modification effect thereof.

In order to achieve the above object, the present inventors have conducted extensive studies. As a result, they have found that a solid taste-modifier comprising curuculin requires less curuculin for taste-modification than a liquid one does; and that a filmy or granular form is effective in achieving the taste-modification effect.

Accordingly, the present invention, which has been completed based on these findings, provides a method for processing a taste-modifier comprising fresh *Curculigo latifolia* fruits, dried fruits thereof or a curuculin-containing material obtained therefrom into a film or granules.

According to the method for processing a taste-modifier of the present invention, the taste-modifier comprising fresh *Curculigo latifolia* fruits, dried fruits thereof or a curuculin-containing material obtained therefrom is processed into a stable form suitable for effectively exhibiting the taste-modification effect of the same.

DETAILED DESCRIPTION OF THE INVENTION

The taste-modifier comprising fresh *Curculigo latifolia* fruits, dried fruits thereof or a curuculin-containing material obtained therefrom may be processed into granules in the following manner. Namely, the taste-modifier is mixed with water, CMC, granulated sugar, beef tallow and other known binders and the resulting mixture is subjected to wet- or dry-granulation. In the case of the wet-granulation, it is preferable to dry the granules thus obtained.

The taste-modifier may be processed into a film in the following manner. Namely, the taste-modifier is mixed with algae, algae extracts, other natural polysaccharides, starch, guar gum, locust bean gum, an alginic acid preparation, other thickners, pectin, carrageenan, gelatin, agar or other gelling agents and water. Then the obtained mixture is formulated into a film by smearing, spraying or extruding followed by drying. In addition to the abovementioned materials, soybean protein, fats, oils and water may be used to thereby give a dried bean curd-type product.

Either the granular product or the filmy one may be preferably dried at a temperature of 90° C. or below.

The particle size of the granules may preferably range from 0.1 to 3 mm, though it is not restricted thereby. When the particle size is excessively large, the taste-modifier would require an undesirably long period of time for adhering to the receptor membranes on the tongue. The granules may be in any shape, for example, spheres or columns, without restriction.

The thickness of the film may preferably range 0.05 to 1 mm, though it is not restricted thereby. When the film is excessively thick, the taste-modifier has a poor contact efficiency with the receptor membranes on the tongue.

The abovementioned granular or filmy product may contain the taste-modifier in such an amount as to give 0.01 mg or more of curuculin, on a pure basis, per intake. The granular or filmy product may generally contain 0.001 to 5% by weight of pure curuculin.

The fresh *Curculigo latifolia* fruits or dried fruits thereof constituting the taste-modifier to be used in the present invention may be preferably free from peels and seeds, since no curuculin is contained in these parts.

The method for drying *Curculigo latifolia* fruits is not particularly restricted. Namely, sun-dried *Curculigo latifolia* fruits, hot air-dried ones and lyophilized ones such as lyophilized pulp may be used in the present invention.

The fresh *Curculigo latifolia* fruits or dried fruits thereof may be generally ground, milled or changed into a paste prior to the use, though the form of the optionally dried *Curculigo latifolia* fruits is not particularly restricted.

Examples of the curuculin-containing material obtained from fresh *Curculigo latifolia* fruits or dried fruits thereof described above include curuculin extracted from fresh *Curculigo latifolia* fruits, dried fruits thereof or the residue obtained by appropriately treating the fresh *Curculigo latifolia* fruits or dried fruits thereof and removing a curuculin-free component therefrom. The concentration of the curuculin extracted from fresh *Curculigo latifolia* fruits or dried fruits thereof is not particularly restricted. Namely, either a highly pure curuculin or an extract containing a large amount of materials other than the curuculin may be used in the present invention. Further the extract may be mixed with other components.

The extraction of the curuculin is not particularly restricted. A preferable example thereof comprises extracting from fresh *Curculigo latifolia* fruits or dried fruits thereof with an aqueous solution of a salt at a concentration of at least 0.01M. Examples of the salt include chlorides such as sodium chloride, potassium chloride, calcium chloride, magnesium chloride and ammonium chloride; phosphates such as sodium phosphate, potassium phosphate, magnesium phosphate and ammonium phosphate; carbonates such as sodium carbonate, potassium carbonate, magnesium carbonate and ammonium carbonate; sulfates such as sodium sulfates, magnesium sulfate, calcium sulfate and ammonium sulfate; sulfites such as sodium sulfites, mangesium sulfite, calcium sulfite and ammonium sulfite; nitrates such as sodium nitrate and potassium nitrate; nitrites such as sodium nitrite and potassium nitrite; lactates such as sodium lactate and calcium lactate; alum; burnt alum; sodium acetate; pyrophosphates such as sodium pyrophosphate and potassium pyrophosphate; propionates such as sodium propionate and calcium propionate; sodium benzoate; sodium fumarate; and sodium polyacrylate.

A typical example of the extraction of curuculin with the aqueous solution of a salt may be carried in the following manner.

An aqueous solution of a salt such as sodium chloride is added to fresh *Curculigo latifolia* fruits or dried fruits thereof and the obtained mixture is homogenized followed by filtering and centrifuging. Since curuculin is contained in the water-insoluble part of *Curculigo latifolia* sarcocarp, it is preferable to homogenize the above mixture of the fresh *Curculigo latifolia* fruits or dried fruits thereof and water followed by thoroughly washing the mixture to thereby remove the water-soluble part and extracting from the residue with the abovementioned salt solution so as to elevate the purity of curuculin.

The concentration of the salt of the aqueous solution to be used for the extraction should be 0.01M or more, since curuculin can not be sufficiently extracted with a salt solution of a concentration lower than 0.01M. On the other hand, a salt solution of an excessively high concentration requires a prolonged period of time for desalting following the extraction. Thus the concentration of the salt solution preferably ranges from 0.1 to 1.0M, from the viewpoints of the extraction efficiency and the subsequent purification procedure.

The extract thus obtained with the use of the salt solution is then desalted and dried to give a curuculin-containing material which is sufficiently available in practice. However the purity of curuculin can be further elevated by purifying the above extract by ion exchange chromatography with the use of CM-Sepharose and HPLC with the use of a gel column followed by desalting and drying. Thus pure curuculin can be obtained. It is a matter of course that the curuculin purity may be further elevated by various purification procedures other than those described above, for example, known protein purification procedures such as salting-out or solvent precipitation.

A typical example of the curuculin thus obtained is a protein having a molecular weight of approximately 12,500 dalton, an amino acid residue number of 97 and an iso-electric point of 7.1. This protein is present as a dimer of a molecular weight of approximately 26,000 dalton. The following Table 1 shows the amino acid composition of this protein. Thus it contains relatively large amounts of aspartic acid, leucine and glycine.

TABLE 1

| Amino acid | | % by mol | No. of residues |
|---|---|---|---|
| Aspartic acid | (Asp) | 17.3 | 17 |
| Threonine | (Thr) | 6.4 | 6 |
| Serine | (Ser) | 7.0 | 7 |
| Glutamic acid | (Glu) | 7.2 | 7 |
| Proline | (Pro) | 1.2 | 1 |
| Glycine | (Gly) | 12.5 | 12 |
| Alanine | (Ala) | 5.3 | 5 |
| Cystine | (Half-cys) | — | — |
| Valine | (Val) | 6.8 | 7 |
| Methionine | (Met) | 0.4 | 1 |
| Isoleucine | (Ile) | 4.2 | 4 |
| Leucine | (Leu) | 14.5 | 14 |
| Tyrosine | (Tyr) | 5.2 | 5 |
| Phenylalanine | (Phe) | 1.3 | 1 |
| Lysine | (Lys) | 2.7 | 3 |
| Histidine | (His) | 2.4 | 2 |
| Arginine | (Arg) | 5.5 | 5 |
| Total | | | 97 |

In the present invention, the taste-modifier is processed into a solid product, namely, a granular or filmy one. The reason therefor is as follows.

In the present invention, the use of fresh *Curculigo latifolia* fruits, dried fruits thereof or crude curuculin obtained therefrom as a taste-modifier is preferred to the use of purified curuculin from the viewpoint of commercial application. However the fresh *Curculigo latifolia* fruits, dried fruits thereof or the crude curuculin obtained therefrom contain proteases and thus have a poor stability, in particular, in the form of an aqueous solution.

The stability thereof may be improved by lowering the moisture activity, namely, formulating it into a solid product or by formulating it into an aqueous solution and UHT-sterilizing or aseptically filling the same. However the former method is preferable, since an aqueous solution requires more curuculin for taste-modification than a solid product does, as will be shown hereinafter. The stability can be further improved by heating the curuculin material to a low temperature during the above procedure.

In the case of an aqueous solution of curuculin, the minimum concentration of pure curuculin required for taste-modification is 0.01%. Namely, 1 ml of the aqueous solution should contain at least 0.1 mg of curuculin. In the case of a solid curuculin material, on the other hand, a sufficient taste-modification effect can be obtained by taking at least 0.1 g of *Curculigo latifolia* sarcocarp or at least 0.01 mg of pure curuculin. Thus the solid product requires less curuculin than the aqueous solution does. This might be caused by the difference in the adhesion ratio to the receptor membranes on the tongue between these products.

The curuculin-containing material may be formulated into various solid forms. A powder is undesirable since it would adhere to everywhere in the oral cavity and thus have a low adhesion ratio to the receptor membranes on the tongue. Thus a bound product is preferable. However a large bound material such as a tablet requires a prolonged period of time for adhering to the receptor membranes on the tongue. Therefore it is preferable to formulate said curuculin-containing material into small particles such as granules or pellets or a film. A film may be used in coating a food whose taste is to be modified. In the case of the composite food product thus obtained, the taste-modifier film would first come in contact with the receptor membranes on the tongue to thereby modify the taste of the content.

To further illustrate the present invention, the following Examples will be given.

EXAMPLE 1

*Curculigo latifolia* fruits were washed with water and peels and seeds werer removed therefrom. The residual sarcocarp was ground.

2% of pullulan and 2% of carrageenan were added to water and dissolved therein by heating to 65° C. In the obtained solution, was dispersed 10% of the ground sarcocarp. The dispersion was homogenized in a mixer, smeared onto a steel belt and dried at 70° C. Thus a film containing the taste-modifier of 0.2 mm in thickness was obtained.

Lemon juice, which was taken following approximately 5 $cm^2$ of this film, tasted preferably sweet.

A pickled ume coated with this film tasted not sour but sweet.

EXAMPLE 2

500 l of water was added to 100 kg of *Curculigo latifolia* sarcocarp ground in the same manner as the one described in Example 1. The obtained mixture was homogenized and centrifuged at 10,000 rpm for 30 minutes. After removing the supernatant, 500 l of water was further added to the residue. Then the mixture was homogenized and centrifuged and the supernatant was removed to thereby give the residue.

The obtained residue was hot air-dried at 70° C. Thus 400 g of a curuculin-containing material was obtained.

400 g of the product, 600 g of lactose and 300 ml of water were introduced into a high-speed mixer (FS-G; mfd. by Fukae Kogyo K. K.), granulated therein and dried under reduced pressure. Thus pellets of 1 mm in diameter were obtained.

Three pellets thus obtained were placed on the tongue and then 0.02M aqueous solution of citric acid was taken. Thus the citric acid solution tasted sweet just like a sugar solution does.

What is claimed is:

1. A method for processing a taste-modifier which comprises formulating a taste-modifier from curuculin which was extracted with an aqueous salt solution from fresh *Curculigo latifolia* fruits or dried fruits thereof, into granules or film and wherein said granules or film is provided with a sufficient taste-modification effect by including at least 0.01 mg of pure curculin into an amount of the granules or film to be used per intake.

2. A method of claim 1 wherein the taste-modifier is formulated as granules.

3. The method of claim 2 wherein the granules are 0.1 to 3 mm.

4. The method of claim 3 wherein the granules are formulated with 0.001 to 5% by weight curuculin.

5. The method of claim 2 wherein the granules are formulated with 0.001 to 5% by weight curuculin.

6. The method of claim 1 wherein the taste-modifier is formulated as a film.

7. The method of claim 6 wherein the film is 0.05 to 1 mm in thickness.

8. The method of claim 7 wherein the film is formulated with 0.001 to 5% by weight curuculin.

9. The method of claim 6 wherein the film is formulated with 0.001 to 5% by weight curuculin.

* * * * *